United States Patent [19]
VanderSlik

[11] Patent Number: 4,976,712
[45] Date of Patent: Dec. 11, 1990

[54] RETAINING SLEEVE FOR SURGICAL PIN

[76] Inventor: Julius VanderSlik, 5264 Green Meadow, Kalamazoo, Mich. 49009

[21] Appl. No.: 502,413

[22] Filed: Mar. 30, 1990

[51] Int. Cl.$^5$ ............................................. A61F 5/04
[52] U.S. Cl. ........................................ 606/59; 606/73
[58] Field of Search ............... 606/59, 54, 96, 57, 606/95, 67, 103, 60, 147, 65, 151, 72, 157, 73, 217, 220; 29/566.3, 566.4; 44/340–345, 438, 512, 521, 525, 526; 24/112, 115 R, 600, DIG. 10, 113 MP, 129 C, 129 W

[56] References Cited
U.S. PATENT DOCUMENTS

| | | | |
|---|---|---|---|
| 2,397,545 | 4/1946 | Hardinge | 606/65 |
| 2,760,488 | 8/1956 | Pierce | 606/72 |
| 3,170,753 | 2/1965 | Witte | 24/115 R |
| 3,602,218 | 8/1971 | Riordan | 606/72 |
| 4,688,560 | 8/1987 | Schultz | 606/73 |
| 4,778,468 | 10/1988 | Hunt | 606/73 |
| 4,860,746 | 8/1989 | Yoon | 128/843 |
| 4,869,242 | 9/1989 | Galluzzo | 606/59 |

Primary Examiner—Robert A. Hafer
Assistant Examiner—Michael Brown
Attorney, Agent, or Firm—Flynn, Thiel, Boutell & Tanis

[57] ABSTRACT

A method and apparatus for treating fractured bones in which a wire is implanted in the body and an exposed end of the wire projects outwardly from the patient's body. A sleeve is placed on the exposed end of the wire and is crimped thereto so that the sleeve will be effective to prevent migration of the wire into the patient's body.

2 Claims, 1 Drawing Sheet

RETAINING SLEEVE FOR SURGICAL PIN

This invention relates to an improved method and apparatus for effecting skeletal fixation of fractured bones in a human or animal body. More particularly, the invention relates to a method and apparatus, as aforesaid, in which one or more Kirschner wires, commonly called "K" wires, or Cerclage wires, commonly called "C" wires, are implanted in the body and then a sleeve is placed on the exposed end of each wire and is crimped thereto and is effective to prevent migration of the wire into the body.

It is well known to use K wires and C wires for the purposes indicated above. K wires and C wires are principally used in the treatment of fractures of small bones of the feet and hands.

A K wire is a round rod made of stainless steel. Generally, it comes in various diameters of 0.6, 0.8, 1.0, 1.25 and 1.6 mm and lengths of approximately 50 mm to approximately 225 mm long. Stainless steel is nonmagnetic, nonporous and easily sterilized. The end of the K wire that penetrates the flesh or bone is sharpened like a three-sided drill. Using a hand-operated drill, a K wire is implanted either in the end of a toe or a finger. This keeps the fractured bone properly aligned during the healing process. The K wire is removed approximately one to two months after the operation, or after healing occurs. Usually the K wire is removed simply by pulling it out of the patient's body.

C wires are similar to K wires, except that, in general, their diameters are smaller.

K wires and C wires can migrate into the body during the healing process. If the K wires and C wires have moved into the body and become inaccessible through the point at which they were originally inserted, it will be necessary to perform a second operation for removing the wire. In order to prevent migration of the wire into the body, in some cases, the surgeon bends the exposed end of the wire so that it is substantially 90° to the original axis of the K-wire and is adapted to bear against the patient's skin. This procedure can cause irritation for the patient at the wound site. It is also known to secure a spherical object, called a Jergen's ball, onto the exposed end of the wire by means of a setscrew. This also is awkward and inconvenient to use and it is necessary to use different balls for different diameter wires. Also, the Jergen's ball applies pressure directly against the wound (insertion) site which is not desirable.

SUMMARY OF THE INVENTION

According to one aspect of the invention, there is provided a method for the skeletal fixation of fractured bones in a human or animal body, in which a Kirschner wire or a Cerclage wire is percutaneously implanted in the human body so that one end of the wire is exposed and projects outwardly from the human body. A sleeve is placed on the exposed end of the wire. The sleeve is comprised of a radially enlarged head and a thin-walled, cylindrical shank. The head is opposed to the body of the patient and is adapted to bear thereagainst, whereas the shank surrounds the exposed portion of the wire. The shank is then crimped to the wire to pinch and press the shank against the wire in order to fixedly unite the sleeve to the exposed end of the wire. The enlarged head is adapted to bear against the body of the patient and prevent migration of the wire inwardly into the patient's body.

According to a second aspect of the invention, there is provided a device for the percutaneous fixation of small fractures in the human body which comprises a Kirschner wire or a Cerclage wire which is adapted to be percutaneously implanted in the human body. A tubular sleeve is comprised of a radially enlarged head at one end thereof and a thin-walled cylindrical shank projecting axially away from the head. The sleeve is adapted to be sleeved on the exposed end portion of the wire, with the head being adapted to bear against the skin of the patient's body and the shank is adapted to be crimped into interlocked relationship with the wire so that the wire is fixedly interconnected to the sleeve and is prevented from migrating into the patient's body.

DETAILED DESCRIPTION

Figure 1:
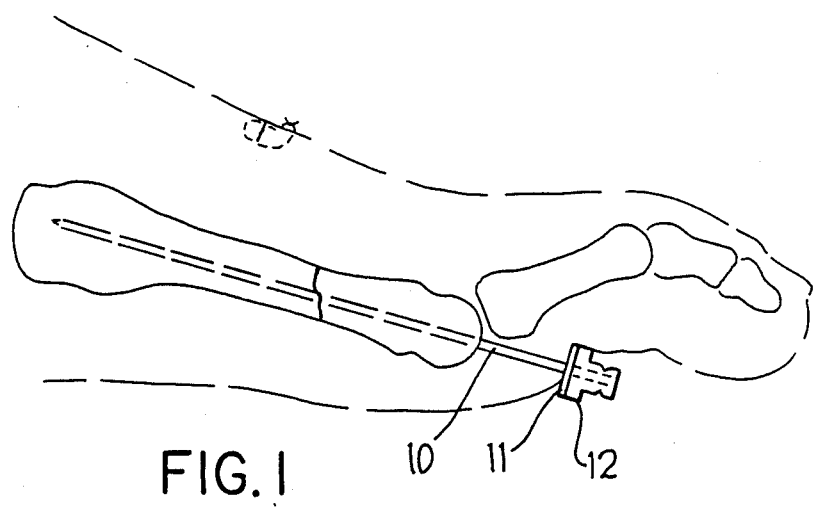
FIG. 1 is a schematic view of the fixation of a metatarsal bone using a K wire, which fixation is representative of a typical way in which the invention is used.

FIG. 1 shows, for illustrative and background purposes only, a fixation of a fractured metatarsal bone using a K wire 10 and a sleeve 12 to prevent migration of the K wire into the patient's body. It will be understood that the invention can be widely used for fixation of fractured bones by means of K wires or C wires, and the invention is not limited to the specific fixation illustrated in FIG. 1.

In general, after the fracture is reduced by the surgeon, the K wire 10 is inserted through a drilled hole in the bone traversing the fracture zone. For this purpose, surgeons commonly use a handchuck for inserting the wire. After the wire 10 has been implanted in the body, the exposed end of the wire is cut off with a wire cutting pliers so as to leave a length of wire of approximately one-quarter of an inch protruding from the skin. A sterile gauze pad 11 is placed over the wire 10 to contact the skin of the patient. Then the sleeve 12 is placed over the exposed end of the wire 12 and is crimped in place thereon, again using the pliers.

Figure 2:
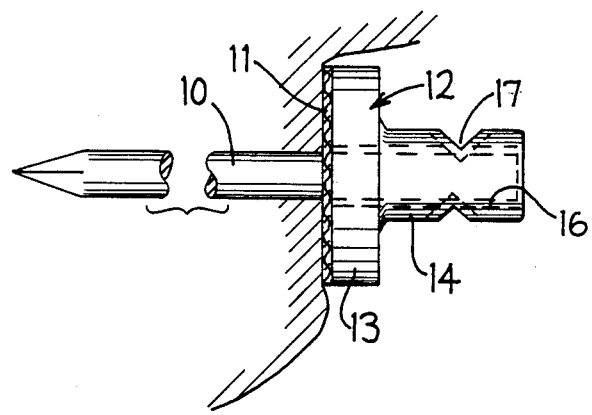
FIG. 2 is an enlarged view of a K wire and a sleeve employed in the invention.

Referring to FIG. 2, the sleeve 12 is substantially T-shaped and is comprised of a radially enlarged head 13 and a thin-walled, cylindrical, axially elongated shank 14 projecting outwardly from the central portion of the head 13. A central passageway is provided to the head 13 and the shank 14. The wire 10 extends through the passageway 16. The diameter of the passageway 16 should be large enough to receive the largest diameter wire with which the sleeve 12 is to be used. For example, the diameter of the passageway can be about 2 mm and the external diameter of the shank 14 can be about 3.2 mm. The diameter of the head 13 can be about 8 mm, the thickness of the head 13 can be about 1.9 mm, and the length of the shank can be about 4.75 mm.

When the shank 14 of the sleeve 12 is crimped onto the wire 10, as indicated at 17, the sleeve is thereby mechanically interlocked with and is affixed against axial movement with respect to the wire 10. The sleeve 12 substantially fully covers the exposed end of the wire 10 and protects the patient from injury.

The sleeve 12 is made of stainless steel, like the K wires and C wires.

The invention provides a simple locking device to prevent the K wire or C wire from migrating into the patient's body after the wire has been implanted in the patient. The locking device is easy to apply and can be routinely applied by the surgeon using the same pliers that he uses for cutting the K-wire.

Although a particular preferred embodiment of the invention has been described, the invention contemplates such changes or modifications therein as lie within the scope of the appended claims.

The embodiments of the invention in which an exclusive property or privilege is claimed are defined as follows:

1. A method for the skeletal fixation of fractured bones in a human or animal body, which comprises the steps of percutaneously implanting a Kirschner wire or Cerclage wire in the body so that an exposed end of said wire projects outwardly from the body; placing on the exposed end of said wire a substantially T-shaped sleeve comprised of a radially enlarged head and a thin-walled, cylindrical shank so that said head is opposed to said body and is adapted to bear thereagainst and said shank surrounds the exposed portion of said wire; and then crimping said shank to pinch and press it against said wire in order to fixedly unite said sleeve to the exposed end of said wire whereby said enlarged head is adapted to bear against the body and prevent migration of said wire into the body.

2. A device for percutaneous fixation of small fractures in a human or animal body, comprising: a wire selected from the group consisting of Kirschner wires and Cerclage wires adapted to be percutaneously implanted in the body; a substantially T-shaped tubular sleeve comprised of a radially enlarged head at one end thereof and adapted to bear against the skin of the body to prevent movement of said sleeve into the body, said sleeve having a thin-walled, cylindrical shank projecting axially away from said head, said sleeve being sleeved on the end portion of said wire with said head being adapted to bear against the skin of the body and with said shank and the outer portion of said wire projecting away from the skin of the body, said shank being crimped into interlocked relationship with said wire so that said wire is fixedly interconnected to said sleeve.

* * * * *